(12) United States Patent
Jung et al.

(10) Patent No.: US 9,918,645 B2
(45) Date of Patent: Mar. 20, 2018

(54) METHOD AND APPARATUS FOR MEASURING CHANGE IN BLOOD PRESSURE BY RESPIRATION CONTROL

(71) Applicant: Samsung Electronics Co., Ltd., Gyeonggi-do (KR)

(72) Inventors: Sun-Tae Jung, Gyeonggi-do (KR); Jae-Geol Cho, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 228 days.

(21) Appl. No.: 13/826,601

(22) Filed: Mar. 14, 2013

(65) Prior Publication Data
US 2014/0031638 A1   Jan. 30, 2014

(30) Foreign Application Priority Data

Jul. 27, 2012 (KR) ........................ 10-2012-0082572

(51) Int. Cl.
| | |
|---|---|
| A61B 5/00 | (2006.01) |
| A61B 5/08 | (2006.01) |
| A61B 5/02 | (2006.01) |
| A61B 5/0205 | (2006.01) |
| A61B 5/021 | (2006.01) |
| A61B 5/0402 | (2006.01) |
| A61B 5/0215 | (2006.01) |
| A61B 5/0225 | (2006.01) |
| A61B 5/024 | (2006.01) |

(52) U.S. Cl.
CPC .......... *A61B 5/0205* (2013.01); *A61B 5/0082* (2013.01); *A61B 5/024* (2013.01); *A61B 5/0215* (2013.01); *A61B 5/0225* (2013.01); *A61B 5/0402* (2013.01); *A61B 5/0816* (2013.01); *A61B 5/486* (2013.01); *A61B 5/4848* (2013.01); *A61B 5/7278* (2013.01); *A61B 5/742* (2013.01)

(58) Field of Classification Search
None
See application file for complete search history.

(56) References Cited

U.S. PATENT DOCUMENTS

| 4,617,937 A | * | 10/1986 | Peel et al. ...................... 600/493 |
| 4,665,926 A | * | 5/1987 | Leuner et al. ................. 600/529 |

(Continued)

FOREIGN PATENT DOCUMENTS

| KR | 1020110071839 | 6/2011 | |
| WO | WO 2012033232 A1 | * 3/2012 | ............. A61B 5/022 |

OTHER PUBLICATIONS

Liu et al., A Wearable Respiratory Biofeedback System Based on Generalized Body Sensor Network, Telemedicine and e-HEALTH Jun. 2011.*

*Primary Examiner* — Gary Jackson
*Assistant Examiner* — Manolis Pahakis
(74) *Attorney, Agent, or Firm* — The Farrell Law Firm, P.C.

(57) ABSTRACT

A method and an apparatus are provided for measuring a change in blood pressure caused by respiration control. A number of respirations per minute is measured based on a heart rate when a respiration exercise begins. Respiration of a subject is induced until the number of respirations per minute reaches a predetermined number of respirations per minute. A pulse transit time is calculated during the respiration exercise, a blood pressure value associated with the pulse transit time is calculated, and the blood pressure value is outputted.

12 Claims, 4 Drawing Sheets

(56) References Cited

U.S. PATENT DOCUMENTS

| | | | | |
|---|---|---|---|---|
| 4,798,538 A * | 1/1989 | Yagi | A61B 5/08 434/262 |
| 4,827,943 A * | 5/1989 | Bornn et al. | 600/481 |
| 5,343,871 A * | 9/1994 | Bittman et al. | 600/545 |
| 5,423,328 A * | 6/1995 | Gavish | 600/534 |
| 5,564,427 A * | 10/1996 | Aso et al. | 600/494 |
| 5,724,983 A * | 3/1998 | Selker | A61B 5/0205 600/301 |
| 5,876,348 A * | 3/1999 | Sugo et al. | 600/490 |
| 5,931,790 A * | 8/1999 | Peel, III | 600/494 |
| 6,047,203 A * | 4/2000 | Sackner et al. | 600/388 |
| 6,081,742 A * | 6/2000 | Amano | A61B 5/0205 600/484 |
| 6,090,037 A * | 7/2000 | Gavish | 600/27 |
| 6,228,033 B1 * | 5/2001 | Koobi et al. | 600/483 |
| 6,662,032 B1 * | 12/2003 | Gavish et al. | 600/323 |
| 6,702,752 B2 * | 3/2004 | Dekker | 600/484 |
| 6,736,789 B1 * | 5/2004 | Spickermann | 604/5.01 |
| 6,805,673 B2 * | 10/2004 | Dekker | A61B 5/0205 600/324 |
| 6,863,656 B2 * | 3/2005 | Lurie | 600/481 |
| 7,117,032 B2 * | 10/2006 | Childre | A61B 5/02405 600/529 |
| 7,314,451 B2 * | 1/2008 | Halperin | A61B 5/113 600/529 |
| 7,338,410 B2 * | 3/2008 | Dardik | 482/13 |
| 7,682,312 B2 * | 3/2010 | Lurie | 600/481 |
| 7,878,198 B2 * | 2/2011 | Farrell | A61B 5/0205 128/204.18 |
| 8,475,370 B2 * | 7/2013 | McCombie et al. | 600/301 |
| 8,506,480 B2 * | 8/2013 | Banet et al. | 600/301 |
| 2003/0028120 A1 * | 2/2003 | Mault | A61B 5/0833 600/531 |
| 2003/0149344 A1 * | 8/2003 | Nizan | A61B 5/486 600/300 |
| 2003/0158466 A1 * | 8/2003 | Lynn | A61B 5/00 600/300 |
| 2003/0167012 A1 * | 9/2003 | Friedman et al. | 600/506 |
| 2004/0030261 A1 * | 2/2004 | Rantala | 600/561 |
| 2004/0116784 A1 * | 6/2004 | Gavish | A61B 5/0205 600/300 |
| 2005/0124906 A1 * | 6/2005 | Childre | A61B 5/02405 600/529 |
| 2005/0148882 A1 * | 7/2005 | Banet | A61B 5/0022 600/485 |
| 2005/0256419 A1 * | 11/2005 | Roach | A61B 5/0205 600/520 |
| 2005/0288728 A1 * | 12/2005 | Libbus | A61N 1/3601 607/42 |
| 2006/0047202 A1 * | 3/2006 | Elliott | A61B 5/0205 600/485 |
| 2006/0229506 A1 * | 10/2006 | Castellanos | A61B 5/02 600/300 |
| 2007/0118054 A1 * | 5/2007 | Pinhas et al. | 600/587 |
| 2007/0203433 A1 * | 8/2007 | Murphy | 601/15 |
| 2008/0035147 A1 * | 2/2008 | Kirby et al. | 128/204.21 |
| 2008/0091111 A1 * | 4/2008 | Shin | A61B 5/0806 600/484 |
| 2008/0319333 A1 * | 12/2008 | Gavish et al. | 600/529 |
| 2009/0216132 A1 * | 8/2009 | Orbach | A61B 5/021 600/485 |
| 2009/0227425 A1 * | 9/2009 | Shirasaki | A61B 5/0205 482/8 |
| 2010/0076511 A1 * | 3/2010 | Heil et al. | 607/9 |
| 2010/0324427 A1 * | 12/2010 | Devot | A61B 5/0205 600/484 |
| 2011/0015468 A1 * | 1/2011 | Aarts | A61B 5/0205 600/26 |
| 2011/0054277 A1 * | 3/2011 | Pinter | A61B 5/0205 600/310 |
| 2011/0152699 A1 | 6/2011 | Cho | |
| 2011/0183305 A1 * | 7/2011 | Orbach | A61B 5/16 434/236 |
| 2011/0190600 A1 * | 8/2011 | McKenna et al. | 600/301 |
| 2011/0288379 A1 * | 11/2011 | Wu | A61B 5/02 600/301 |
| 2011/0301477 A1 * | 12/2011 | Hughes | A61B 5/0205 600/500 |
| 2012/0290266 A1 * | 11/2012 | Jain | G06F 19/3406 702/187 |
| 2013/0165800 A1 * | 6/2013 | Shimizu | A61B 5/022 600/485 |
| 2014/0107493 A1 * | 4/2014 | Yuen | H04W 4/027 600/473 |

* cited by examiner

METHOD AND APPARATUS FOR MEASURING CHANGE IN BLOOD PRESSURE BY RESPIRATION CONTROL

PRIORITY

This application claims the priority under 35 U.S.C. § 119(a) to Korean Application Serial No. 10-2012-0082572, which was filed in the Korean Intellectual Property Office on Jul. 27, 2012, the content of which is incorporated herein by reference.

BACKGROUND OF THE INVENTION

1. Field of the Invention

The present invention relates generally to a blood pressure measuring method and apparatus, and more particularly, to a blood pressure measuring method and apparatus capable of measuring a change in a blood pressure by respiration control.

2. Description of the Related Art

Regular blood pressure measurements may be used to diagnose and treat hypertension and the like.

Most automatic electric blood pressure meters are based on an oscillometry method. The oscillometry method is a scheme for measuring blood pressure based on oscillation generated when an artery is pressurized/depressurized using a cuff. A cuff pressure, when a pulse from a heartbeat has a maximum amplitude, is estimated as an average blood pressure.

For a subject having hypertension, a method for decreasing blood pressure is also important. A method that is generally used to decrease blood pressure includes medication, dietary treatment, exercise, and the like. It is also known that a method of inducing a decrease in blood pressure through respiration control is effective and does not cause side effects. Accordingly, a device for decreasing blood pressure through respiration exercise has been utilized. A sensor strip, which senses a strain on a person's abdomen, is used to measure respiration by sensing movement of the sensor strip. In addition, a number of respirations may be measured based on air-flow exiting the person's mouth, using a non-contact microphone.

Conventionally, a scheme for measuring blood pressure and a scheme for measuring respiration are performed by separate measuring devices. Therefore, although blood pressure is decreased by adjusting respiration, the current blood pressure measuring method does not consider applying the scheme for measuring respiration. A cuff-type blood pressure meter operates by pressurizing a cuff once and depressurizing the cuff and thus, may have difficulty in continuously measuring blood pressure during respiration. Therefore, to measure effectiveness of an exercise in decreasing blood pressure, different devices, such as a blood pressure meter, a respiration measuring device, and the like, are used, which may be inconvenient for a subject. The subject may not directly compare an initial blood pressure measurement result and a blood pressure measurement result after respiration control and thus, may not directly recognize the effectiveness associated with a change in blood pressure through the respiration control. Accordingly, the subject has difficulty in determining a degree of a change in blood pressure occurring in the body a predetermined time after the respiration exercise begins.

SUMMARY OF THE INVENTION

The present invention has been made to address at least the above problems and/or disadvantages and to provide at least the advantages described below. Accordingly, an aspect of the present invention provides a method and an apparatus for measuring blood pressure and respiration using a single measuring device.

Another aspect of the present invention provides a method and an apparatus for measuring a change in blood pressure by respiration control.

In accordance with an aspect of the present invention, a blood pressure measuring apparatus is provided for measuring a change in blood pressure caused by respiration control. The apparatus includes a blood pressure measuring module for measuring blood pressure by pressurizing and depressurizing a cuff. The apparatus also includes a controller for measuring a number of respirations per minute based on a heart rate when a respiration exercise begins, inducing respiration of a subject until the number of respirations per minute reaches a predetermined number of respirations per minute, calculating a pulse transit time during the respiration exercise, and calculating and outputting a blood pressure value associated with the pulse transit time.

In accordance with another aspect of the present invention, a method is provided for measuring a change in blood pressure caused by respiration control in a blood pressure measuring apparatus. A number of respirations per minute is measured based on a heart rate when a respiration exercise begins. Respiration of a subject is induced until the number of respirations per minute reaches a predetermined number of respirations per minute. A pulse transit time is calculated during the respiration exercise, a blood pressure value associated with the pulse transit time is calculated, and the blood pressure value is outputted.

BRIEF DESCRIPTION OF THE DRAWINGS

The above and other aspects, features, and advantages of the present invention will be more apparent from the following detailed description when taken in conjunction with the accompanying drawings, in which.

DETAILED DESCRIPTION OF EMBODIMENTS OF THE PRESENT INVENTION

Figure 1:
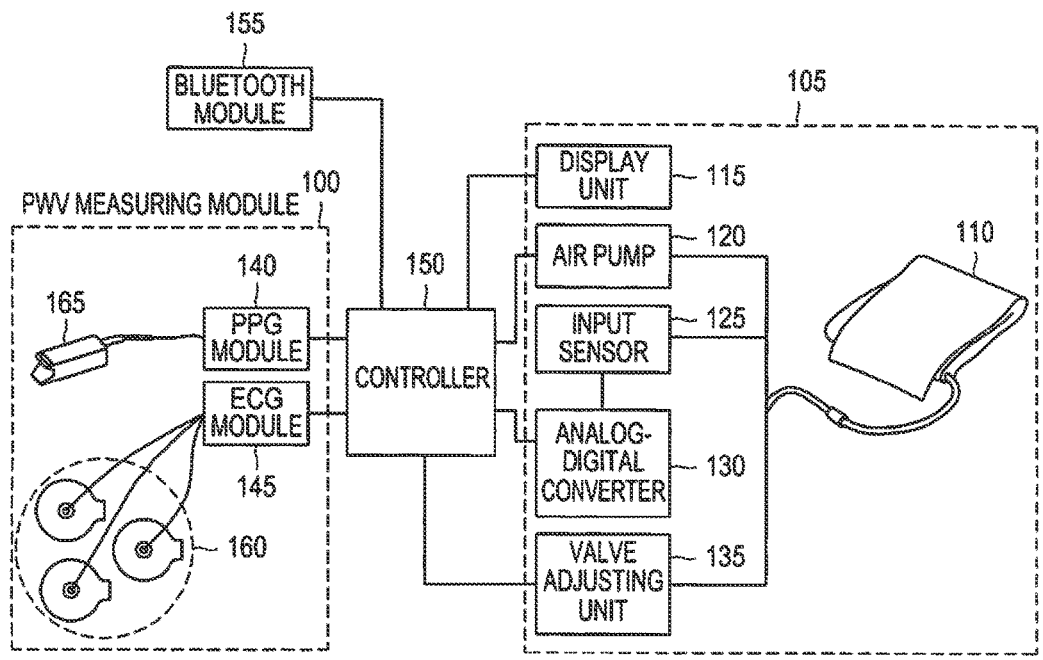
FIG. 1 is a block diagram illustrating a blood pressure measuring apparatus that measures a change in blood pressure by respiration control, according to an embodiment of the present invention.

Embodiments of the present invention are described in detail with reference to the accompanying drawings. The same or similar components may be designated by the same or similar reference numerals although they are illustrated in different drawings. Further, various specific definitions found in the following description are provided only to assist in a general understanding of the present invention, and it is apparent to those skilled in the art that the present invention can be implemented without such definitions. Detailed descriptions of constructions or processes known in the art may be omitted to avoid obscuring the subject matter of the present invention.

The present invention provides a method of measuring a change in blood pressure by respiration control. In order to achieve this, in an embodiment of the present invention, a blood pressure measuring apparatus draws and stores a correlation equation between blood pressure measured by pressurizing a cuff before a respiration exercise and a Pulse Transit Time (PTT) calculated using a pulse wave and an ECG signal. Subsequently, during the respiration exercise, the blood pressure measuring apparatus calculates a PTT and a heart rate using a pulse wave signal and an ECG signal in a state where the cuff is removed, measures a number of respirations per minute using the heart rate, induces respiration to reach a desired number of respirations per minute, and calculates a blood pressure value associated with the calculated PTT based on the correlation equation after respiration reaches the desired number of respirations per minute. Accordingly, a subject may recognize a blood pressure measurement result before a respiration exercise is performed and a change in blood pressure by respiration during the respiration exercise.

Pulse Wave Velocity (PWV), which is used in embodiments of the present invention, is described below. The PTT refers to a time expended between blood leaving a heart and arriving an extremity, such as, for example, a fingertip or a tiptoe. The PTT may be calculated based on an ECG signal and a pulse wave signal.

In blood pressure measurement, a PTT increases as a cuff pressure P (mmHg) increases. A value of a PTT and an increase in the PTT caused by pressure may be different for each subject. The PTT is dependent upon an internal pressure of a blood vessel, a blood vessel thickness, a blood vessel diameter, and an elasticity of a blood vessel. Specifically, the PTT varies when the internal pressure of the blood vessel is changed by a cuff pressure. When the cuff is not used, the internal pressure of the blood vessel has the same value as an average blood pressure. However, when the cuff pressure increases, the internal pressure of the blood pressure decreases. When the cuff pressure continuously increases and becomes equal to the average blood pressure, the internal pressure of the blood vessel becomes 0.

A length of a blood vessel refers to a distance from a heart to an extremity where a pulse wave is measured. In a case where a PTT is calculated when a pressure is not applied, a length of a section where pressure is applied is calculated when the pressure is applied, and a PTT in the pressure-applied section is calculated, blood pressure of each subject may be calculated using the PTT values measured by changing a cuff pressure. A method of measuring blood pressure by measuring a pulse wave, without using a cuff, during a respiration exercise is described in greater detail below.

According to embodiments of the present invention, a blood pressure is measured before a respiration exercise in a state where a cuff is pressurized, a number of respirations per minute is induced to reach a desired number of respirations per minute in a state where the cuff is removed during the respiration exercise, and only a PTT is calculated after the respiration exercise, where the number of respirations per minute reaches the desired number of respirations per minute, so as to estimate successive changes in a blood pressure through a correlation equation stored in advance. As described in the foregoing, according to embodiments of the present invention, a subject measures a blood pressure and performs a respiration exercise using the same measuring device, and may compare blood pressure measurement results before and after the respiration exercise. A blood pressure value, estimated as a respiration exercise progresses, may be output through a display unit 115 of FIG. 1. The subject also measures blood pressure by winding a cuff again so as to recognize a degree of a change in a blood pressure when the respiration exercise is completed. A blood pressure value measured before the respiration exercise, a blood pressure value measured during the respiration exercise, and a blood pressure value measured after the respiration exercise are output as a blood pressure measurement result. Accordingly, the subject may obtain a more accurate blood pressure measurement result associated with the respiration exercise. A configuration of a blood pressure measuring apparatus for measuring a change in blood pressure by respiration control, which embodies the described functions, is described in detail with reference to FIG. 1. According to an embodiment of the present invention, a PTT measuring sensor and a function for measuring respiration are added to an oscillometry-type electric blood pressure measuring apparatus.

FIG. 1 is a block diagram illustrating a blood pressure measuring apparatus that measures a change in blood pressure by respiration control, according to an embodiment of the present invention. A blood pressure measuring apparatus includes a PWV measuring module 100 and a blood pressure measuring module 105.

The blood pressure measuring module 105 has a configuration similar to that of an oscillometry-type blood pressure meter. The blood pressure measuring module 105 measures a blood pressure based on an oscillation generated by pressurizing/depressurizing an artery using a cuff 110. The blood pressure measuring module 105 estimates, as an average blood pressure, a cuff pressure when a pulse by a heart beat has a maximum amplitude. Accordingly, the blood pressure measuring module 105 includes a display unit 115, an air pump 120, a input sensor 125, an analog-digital converter 130, and a valve adjusting unit 135.

The cuff 110 is used to intercept or adjust a flow of an artery. The display unit 115 displays a blood pressure measurement result, an elasticity of a blood vessel, and the like. The air pump 120 pressurizes the cuff 110. The input sensor 125 detects a pressure and converts the pressure into an electric signal through the analog-digital converter 130. The valve adjusting unit 135 depressurizes the cuff 110, and may be configured to be manually adjusted or automatically controlled.

The PWV measuring module 100 includes a PPG module 140 and an ECG module 145. The PPG module 140 is a sensor for detecting a PPG of a subject, specifically, a pulse wave signal, using, for example, a clip-type photo sensor 165 attached to a fingertip. The clip-type photo sensor 165 is configured to measure a pulse wave signal, includes at least one light source that enables a light to be incident to skin and at least one light detector for detecting light coming off of the skin due to dispersion after the incidence of the light to the skin. The pulse wave signal is transferred to a controller 150 to calculate a PTT. The ECG module 145 receives an ECG signal of the subject through the ECG electrodes 160, and transfers the ECG signal to the controller 150. Although FIG. 1 illustrates patch-type electrodes as the ECG electrodes 160 and illustrates a finger-transparent sensor as a sensor for measuring a pulse wave, different sensors that are capable of performing equivalent functions may also be used.

The blood pressure measuring apparatus of FIG. 1 also includes a Bluetooth module 155, as a wireless transceiving unit, that provides the subject with blood pressure measurement values calculated before/after a respiration exercise through a communication medium such as, for example, a portable phone, a Personal Digital Assistant (PDA), a Personal Computer (PC), and the like. The blood pressure measuring apparatus may also include an input unit that receives information such as, for example, a gender of a user, a height of the user, and the like, when calculating a PTT. The input unit may also receive information through the Bluetooth module 155.

The blood pressure measuring apparatus, configured as described above, may be installed, for example, by winding the cuff 110 around an upper arm of the subject, attaching a photo sensor onto a fingertip of the arm where the cuff 110 is wound, and placing electrodes, for measuring an ECG, in contact with a body of the subject, desirably, on both arms or both hands of the subject. Through such an installation, a blood pressure of the subject and a PWV may be simultaneously measured.

The controller 150 calculates a PTT using an ECG signal measured by the ECG module 145 and a pulse wave signal measured by the PPG module 140 in a state where the cuff 110 is pressurized. The PTT is calculated by dividing a length of a blood vessel L by a PWV. The PTT may be continuously or discontinuously measured by controlling the air pump 120 and the valve adjusting unit 135. In this example, the controller 150 may be provided with a blood pressure measurement value when the cuff 110 is pressurized through a signal received by the analog-digital converter 130. Subsequently, the controller 150 draws a correlation equation between the calculated PTT and a blood pressure. For example, the correlation equation corresponds to a relational equation between the calculated PTT and the measured blood pressure value. When the correlation equation is drawn, a blood pressure value may be calculated only using a PTT, without measuring a blood pressure using an actual cuff. Also, the controller 150 uses an ECG signal from the ECG module 145 to measure a respiration. In general, a heart rate increases when the subject inhales during the respiration and a heart rate decreases when the subject exhales. The controller 150 may also use a pulse wave signal from the PPG module 140 to measure a respiration. Measurement of a respiration is performed in a state where the cuff 110 is removed so that a change in a blood pressure is inferred for each successive heart beat.

A change in a heart rate may be measured using an ECG signal or a pulse wave signal. A section where a heart rate increases within a predetermined period of time corresponds to an inhalation section, and a section where the heart rate decreases within a predetermined period of time corresponds to an exhalation section. The controller 150 may measure a number of respirations per minute by detecting a change in heart rate based on a predetermined time unit, for example, based on a unit of one minute. When the number of respirations per minute is greater than a desired number of respirations, the controller 150 induces the subject to breathe slowly. The desired number of respirations per minute is used as a criterion for determining whether the subject breathes slowly. Accordingly, the controller 150 induces respiration until a number of respirations per minute measured during a predetermined period of time reaches the desired number of respirations per minute.

The controller 150 slowly induces a change in the number of respirations to reduce an initially measured number of respirations per minute to the desired number of respirations, for example, 10 times per minute. In this example, various schemes may be used to induce respiration. For example, a number of respirations required to be reduced to within a minute may be calculated by dividing the initially measured number of respirations per minute by a desired number of respirations per minute after 15 minutes. The calculated number of respirations may be displayed as a bar-type indicator on the display unit 115. As another example, a respiration exercise state, such as an arrival rate from a current number of respirations per minute to a desired number of respirations per minute and the like, is displayed or provided through a speaker. Respiration inducement encourages the subject to breathe stably and slowly so as to reduce blood pressure. Thus, various respiration inducements may be used. For example, the subject may set a desired number of respirations and a degree of a change, and may use a method for meditational breathing in addition to the standardized formula.

When the number of respirations per minute reaches the desired number of respirations per minute, the controller 150 considers the respiration exercise complete. Also, during the respiration exercise, a number of respirations may be measured through a change in a heart rate using an ECG signal or a pulse wave signal during the respiration exercise, and a PTT is calculated simultaneously. Accordingly, the controller 150 calculates a blood pressure value by substituting the calculated PTT in a correlation equation stored in advance. During the respiration exercise, successive changes in a blood pressure value may be estimated using the correlation equation by calculating only a PTT by measuring an ECG signal and a pulse wave signal. Therefore, although a conventional cuff-type blood pressure meter has difficulty in continuously measuring a blood pressure, a blood pressure measuring method according to embodiments of the present invention uses only a PTT and thus, may infer a change in a blood pressure for each heart beat and may monitor a change in a blood pressure during a respiration exercise.

Subsequently, a process of measuring a blood pressure using the cuff 110 may be performed after the respiration exercise is completed. This may be performed to compare a result of the respiration exercise with a blood pressure before the respiration exercise, and the subject may select whether to perform the process. When an additional blood pressure measurement is set to be performed by the subject, the controller 150 instructs the subject to measure a blood pressure again in a state where the subject winds the cuff 110 around an upper arm. The instruction may be output through the display unit 115 or the speaker. The blood pressure may be measured when the cuff 110 is pressurized. Subsequently, the controller 150 outputs a blood pressure measurement result before the respiration exercise and a blood pressure measurement result after the respiration exercise. Therefore, the subject may directly determine a change in a blood pressure by respiration control.

Figure 3:
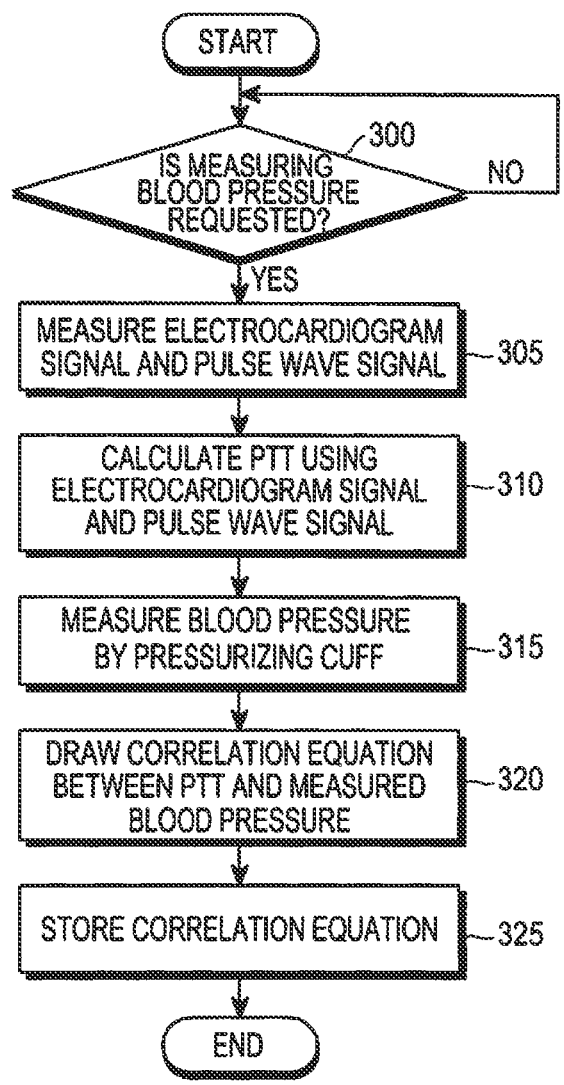
FIG. 3 is a flowchart illustrating a process of drawing a correlation between a pulse transit time before a respiration exercise and blood pressure, according to an embodiment of the present invention.

A process of drawing a correlation equation between a PTT and blood pressure is described in detail below with reference to FIG. 3. Specifically, FIG. 3 is a flowchart illustrating a process of drawing a correlation between a pulse transit time before a respiration exercise and blood pressure, according to an embodiment of the present invention Before executing a respiration exercise application, in embodiments of the present invention, a PTT used for calculating a blood pressure value may be different for each individual and thus, a correlation between a blood pressure value and a PTT may need to be recognized in advance. A subject measures a blood pressure in advance by winding the cuff 110 around an upper arm after turning on a blood pressure measuring apparatus.

It is determined whether blood pressure measurement is requested, in step 300. The blood pressure measuring apparatus measures an ECG signal and a pulse wave signal, in step 305, when a blood pressure measurement request is input from the subject. For example, when the ECG electrode 160 is provided as a finger-transparent sensor, the subject puts both thumbs into a finger-transparent sensor of the ECG module 145, puts a finger of one hand into a finger-transparent sensor of the PPG module 140, and presses a start button for measuring a blood pressure. Accordingly, the PPG module 140 and the ECG module 145 are driven and thus, a pulse wave signal and an ECG signal are detected.

The blood pressure measuring apparatus calculates a PTT using the ECG signal and the pulse wave signal, in step 310, and measures a blood pressure at an upper arm by pressuring the cuff 110, in step 315. When the blood pressure value is measured, a correlation between the measured blood pressure value and the calculated PTT may be recognized. Accordingly, a correlation equation between the measured blood pressure value and the calculated PTT may be drawn, in step 320. Subsequently, the blood pressure measuring apparatus customizes and stores a regression equation indicating the correlation between the blood pressure value and the PTT, in step 325. The regression equation may be applied when the blood pressure value is calculated using the PTT.

As described above, the blood pressure measuring apparatus generates a regression equation corresponding to a relationship between a PTT and a blood pressure value at an initial stage and thus, the blood pressure measuring apparatus may be capable of comparing blood pressure measurement results associated with the subject before/after a respiration exercise. Also, a process of analyzing a relationship between a PTT and a blood pressure value may be changed. More specifically, the process may be performed once for each subject when a blood pressure is initially measured or may be performed once a day or repeatedly performed every time a blood pressure is measured.

Figure 4A:
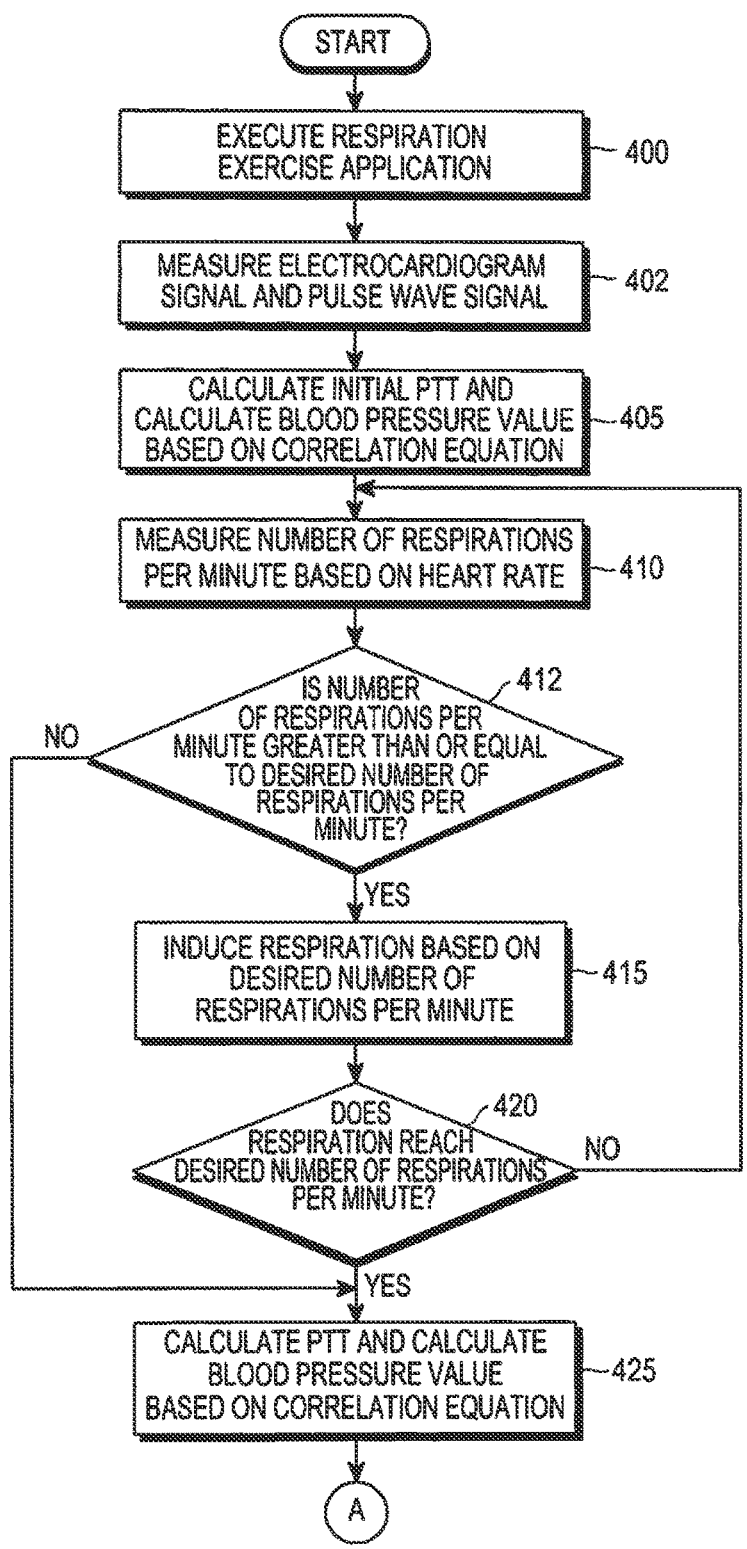
FIGS. 4A and 4B are flowcharts illustrating a process of measuring a change in blood pressure by respiration control, according to an embodiment of the present invention.
Figure 4B:
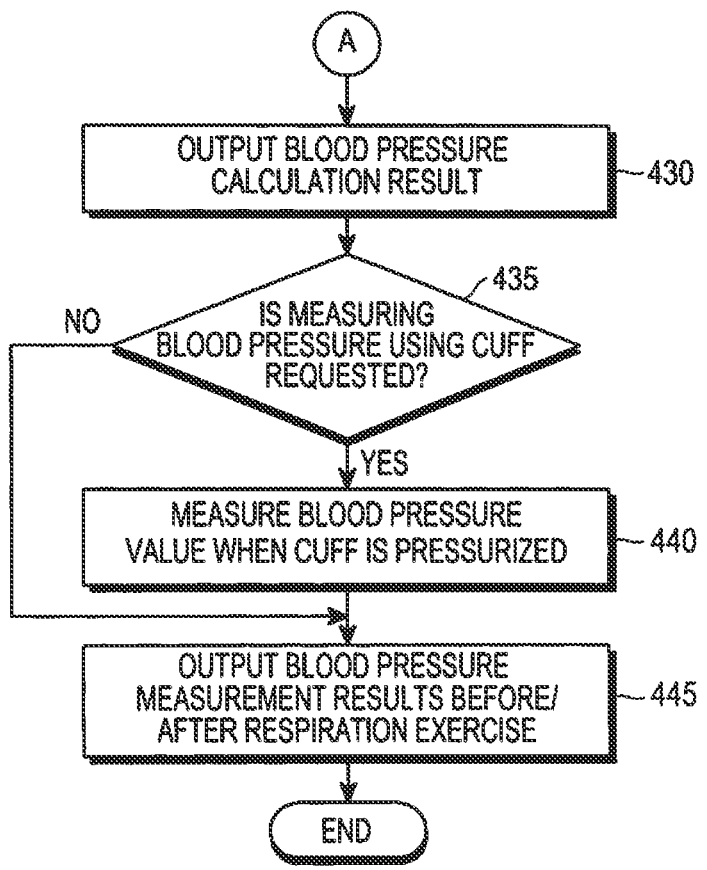

A method of measuring a change in a blood pressure by respiration control is described in detail below with reference to FIGS. 4A and 4B. Specifically, FIGS. 4A and 4B are flowcharts illustrating a process of measuring a change in blood pressure by respiration control, according to an embodiment of the present invention Referring to FIG. 4A, a respiration exercise application is executed, in step 400, and a blood pressure measuring apparatus measures an ECG signal and a pulse wave signal, in step 402. In this embodiment of the present invention, during the respiration exercise, a PTT and a blood pressure value may be calculated in a state where the cuff 110 is removed. Accordingly, the blood pressure measuring apparatus calculates an initial PTT ($PTT_0$) using the ECG signal and the pulse wave signal, in step 405, and calculates a blood pressure value using a correlation equation. A method of calculating $PTT_0$ is described with reference to FIG. 2.

Figure 2:
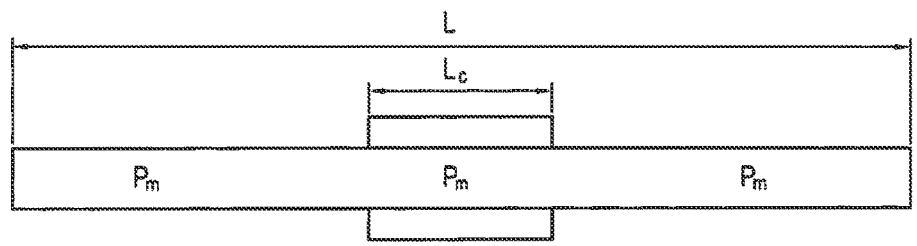
FIG. 2 is a flowchart illustrating a process of measuring blood pressure before a respiration exercise, according to an embodiment of the present invention.

FIG. 2 is a flowchart illustrating a process of measuring blood pressure before a respiration exercise, according to an embodiment of the present invention. Specifically, FIG. 2 illustrates a case in which an artery of which an internal pressure of a blood vessel, that is, an average blood pressure, is $P_m$ and a length of the blood vessel L is pressurized using a cuff having a length $L_c$ (cm). In particular, FIG. 2 illustrates a method of calculating an initial PTT when the cuff is not pressurized. An internal pressure of a blood vessel in a section where a cuff is used may be an average blood pressure $P_m$, which is the same as an average blood pressure in a section where the cuff is not used. The average blood pressure $P_m$ may be calculated from a systolic blood pressure, a diastolic blood pressure, and a blood pressure waveform, as expressed by Equation (1).

$$P_m = P_d + k(P_s - P_d) \quad (1)$$

In Equation (1), $P_d$ denotes a diastolic blood pressure, $P_s$ denotes a systolic blood pressure, and k denotes a waveform coefficient. Here, ⅓ is generally used as the waveform coefficient k.

$$PTT_0 = L\sqrt{\frac{2\rho R}{E_0 h}} \exp\left(-\frac{\alpha}{2}P_m\right) \quad (2)$$

In Equation (2), L, corresponding to a length of an artery, indicates a distance from a heart to a fingertip where a pulse wave is measured. $E_0$ denotes a Young's modulus when a cuff pressure is 0, α is a constant corresponding to a modulus of elasticity of a blood vessel, $P_m$ denotes an average blood pressure, R denotes blood vessel radius, h denotes a wall thickness, and ρ denotes a blood density. Here, L may be calculated by an actual measurement, and may be calculated based on a regression equation using a subject's gender and height. An example of the regression equation is set forth in Equation (3), and the regression equation used in the embodiments of the present invention may not be limited thereto.

$$L = 0.4861 \times \text{Height} + 0.6337 (\text{cm}) \quad (3)$$

Equation (3) corresponds to a regression equation indicating a length from a heart of a Korean male to a finger.

An average blood pressure may be calculated based on Equation (1), $PTT_0$ may be calculated using an ECG signal and a pulse wave signal after substituting the average blood pressure $P_m$ in Equation (2) in the same manner as step 305, and a blood pressure value may be calculated using the calculated $PTT_0$. To calculate the blood pressure value, a correlation equation indicating a relationship between a PTT and blood pressure, stored in advance through the process of FIG. 3, may be used. In this embodiment of the present invention, the blood pressure measuring apparatus may calculate a heart rate in addition to $PTT_0$, using the pulse wave signal and the ECG signal. Accordingly, the blood pressure measuring apparatus measures a number of respirations per minute using a heart rate, in step 410, and determines whether the measured number of respirations per minute is greater than or equal to a desired number of respirations per minute, in step 412. Specifically, it is determined whether the measured number of respirations per minute is greater than the desired number of respirations per minute, which is a criterion for determining slow respiration. When the measured number of respirations is less than the desired number of respirations per minute, it indicates a slow respiration state and thus, the blood pressure measuring apparatus proceeds to step 425.

Conversely, when the number of respirations per minute is greater than or equal to the desired number of respirations per minute in step 412, the blood pressure measuring apparatus may induce respiration based on the desired number of respirations, in step 415. For example, the blood pressure measuring apparatus may output contents inducing slow respiration through the display unit 115 or output a sound guidance to induce slow respiration through a speaker. Subsequently, the blood pressure measuring apparatus determines whether the measured number of respirations per minute reaches the desired number of respirations per minute, in step 420. A number of respirations per minute is repeatedly measured based on a predetermined time unit, while respiration is induced.

When the measured number of respirations per minute does not reach the desired number of respirations per minute, the blood pressure measuring apparatus returns to step 410 and performs the described process. Conversely, when the measured number of respirations per minute reaches the desired number of respirations per minute, the blood pressure measuring apparatus calculates a PTT again using a pulse signal and an ECG signal, in step 425, and calculates a blood pressure value associated with a change in the PTT using the correlation equation. A reference code 'A' is used to indicate that the process proceeds from step 425 of FIG. 4A to step 430 of FIG. 4B.

Accordingly, the blood pressure measuring apparatus outputs a blood pressure value calculation result, in step 430 of FIG. 4B. As described in the foregoing, according to embodiments of the present invention, a PTT and a blood pressure value are repeatedly calculated and displayed at regular intervals during a respiration exercise and thus, a subject is informed of a change in the blood pressure value by respiration. The function of displaying the change in the blood pressure at regular intervals during the respiration exercise may be optionally set by the subject.

As described in the foregoing, when the measured number of respirations per minute reaches the desired number of respirations per minute, this indicates that a respiration exercise for decreasing a blood pressure has been completed. The subject may desire to measure a blood pressure after the respiration exercise is completed so as to compare the blood pressure with a blood pressure measurement result before the respiration exercise, and the additional blood pressure of is optionally performed.

When the subject sets additional blood pressure measurement to be performed after the respiration exercise is completed, the blood pressure measuring apparatus informs the subject of a request for measuring a blood pressure using the cuff 110 through the display unit 115, a speaker, or the like. When the subject desires to recognize a change in a blood pressure associated with a respiration exercise result, the subject may measure a blood pressure using the cuff 110.

Accordingly, the subject winds the cuff 110 around an upper arm and puts fingers into corresponding sensors 160 and 165, and presses a start button or the like, so as to request measuring a blood pressure, in the same manner as the blood pressure measurement performed before the respiration exercise. The blood pressure measuring apparatus determines whether a blood pressure measurement using the cuff 110 is requested, in step 435. When the request for measuring a blood pressure using the cuff 110 exists, the blood pressure measuring apparatus may measure a blood pressure when the cuff 110 is pressurized, in step 440. Conversely, when the request for measuring a blood pressure using the cuff 110 does not exist, blood pressure measurement results before/after the respiration exercise are output, in step 445. Accordingly, a blood pressure value before the respiration exercise and a blood pressure value after the respiration exercise are displayed on the display unit 115, and various information associated with blood pressure measurement during a respiration exercise and the like may be displayed. Therefore, the subject may accurately recognize a change in blood pressure before/after a respiration exercise. Although embodiments of the present invention describe a case in which a blood pressure measurement result associated with a respiration exercise is displayed on the display unit 115 of the blood pressure measuring apparatus, information associated with blood pressure measurement may be provided through other devices that operate in conjunction with the blood pressure measuring apparatus, using an application installed in the other devices, such as, for example, a smart phone, a tablet PC, a smart TV, and the like. The application may receive data associated with blood pressure measurement from the blood pressure measuring apparatus and may manage the received data.

As described in the foregoing, in FIGS. 4A and 4B, blood pressure of the subject before a respiration exercise is measured in advance and thus, blood pressure measurement results before/after a respiration exercise may be output. Also, a PTT may be calculated and blood pressure may be measured during the respiration exercise. Thus, a change in a blood pressure by respiration may be shown without measuring a blood pressure using a cuff.

Therefore, according to embodiments of the present invention, blood pressure and respiration may be measured using a single measuring device and thus, a subject may recognize a change in a blood pressure from respiration exercise without changing a device.

According to embodiments of the present invention, a blood pressure measuring function and a respiration measuring function for adjusting a blood pressure are embodied by an integrated device. The device is portable and is easy for storage, and improves user convenience. Also, the embodiments of the present invention enable measuring of blood pressure and respiration simultaneously in an integrated blood pressure measuring apparatus corresponding to a hardware-type blood pressure meter to which a software-type respiration measuring function is applied and thus, a user may immediately recognize a change in a blood pressure and a PWV by respiration control. Accordingly, effectiveness of the respiration exercise may be more improved and motivation may be provided.

In addition, the blood pressure measuring apparatus, according to embodiments of the present invention may record and store measured blood pressure data and may output a result through an application that operates in conjunction with various devices such as, for example, a smart phone, a tablet PC, a smart TV, and the like, and may utilize the data by connecting various additional information and thus, may extend the use of the blood pressure measuring apparatus.

While the present invention has been shown and described with reference to certain embodiments thereof, it will be understood by those skilled in the art that various changes in form and detail may be made therein without departing from the spirit and scope of the present invention as defined by the appended claims.

What is claimed is:

1. A blood pressure measuring apparatus for measuring a change in blood pressure caused by respiration control exercise, the apparatus comprising:
   a display unit;
   an oscillometric blood pressure meter having a cuff;
   a PhotoPlethysmoGraphy (PPG) sensor;
   an ElectroCardioGram (ECG) sensor; and
   a controller configured to:
   pressurize the cuff of the oscillometric blood pressure meter and measure a first blood pressure value with the oscillometric blood pressure meter, a first pulse wave signal with the PPG sensor, and a first ECG signal with the ECG sensor;
   calculate a first pulse transit time based on the first pulse wave signal and the first ECG signal;
   draw and store a correlation equation between the first blood pressure and the first pulse transit time;
   continuously:
   measure a second pulse wave signal with the PPG sensor and a second ECG signal with the ECG sensor;

measure a number of respirations per minute based on the second pulse wave signal measured with the PPG sensor or the second ECG signal measured with the ECG sensor;

calculate a second pulse transit time based on the second pulse wave signal and the second ECG signal;

determine whether the measured number of respirations per minute is greater than or equal to a predetermined number of respirations per minute;

display, on the display unit, information for inducing respiration of the subject until the number of respirations per minute reaches the predetermined number of respirations per minute, the information including the predetermined number of respirations per minute or a difference between the predetermined number of respirations per minute and the measured number of respirations per minute;

calculate a second blood pressure value based on the second calculated pulse transit time and the stored correlation equation, when the measured number of respirations per minute is greater than the predetermined number of respirations per minute, and output the calculated second blood pressure value; and measure a third pulse transit time with the PPG and ECG sensors and calculate a third blood pressure value based on the third pulse transit time and the stored correlation equation, when the measured number of respirations per minute reaches the predetermined number of respirations per minute;

display, on the display unit, the first and third blood pressure value, after the measured number of respirations reaches the predetermined number of respirations.

2. The apparatus of claim 1, wherein the controller calculates a heart rate using the pulse wave signal or the ECG signal and measures the number of respirations per minute based on the heart rate.

3. The apparatus of claim 1, wherein when the controller calculates the pulse transit time, the cuff is removed, and
wherein the controller calculates the blood pressure value by substituting the pulse transit time in the correlation equation.

4. The apparatus of claim 1, wherein the controller outputs the calculated blood pressure value when the measured number of respirations per minute is greater than or equal to the predetermined number of respirations per minute.

5. The apparatus of claim 1, wherein the controller outputs a blood pressure measurement result including at least one of a blood pressure value measured before the respiration exercise and a blood pressure value calculated during the respiration exercise, when the measured number of respirations per minute is greater than or equal to the predetermined number of respirations per minute.

6. The apparatus of claim 1, wherein when controller measures the number of respirations per minute, the cuff is not pressurized.

7. The apparatus of claim 1, further comprising:
a speaker to output a sound guidance to induce respiration of the subject until the measured number of respirations per minute corresponds to the predetermined number of respirations per minute.

8. A method of measuring a change in blood pressure caused by respiration control exercise with a blood pressure measuring apparatus, the method comprising the steps of:

measuring a first blood pressure value with an oscillometric blood pressure meter of the apparatus, the oscillometric blood pressure meter having a cuff;

measuring a first pulse wave signal with a PhotoPlethysmoGraphy (PPG) sensor of the apparatus;

measuring a first ElectroCardioGram (ECG) signal with an ECG sensor of the apparatus;

calculating a first pulse transit time based on the first pulse wave signal and the first ECG signal;

drawing and storing a correlation equation between the first blood pressure and the first pulse transit time;

continuously:
measuring a second pulse wave signal with the PPG sensor and a second ECG signal with the ECG sensor;

measuring a number of respirations per minute based on the second pulse wave signal measured with the PPG sensor or the second ECG signal measured with the ECG sensor;

calculating a second pulse transit time based on the second pulse wave signal and the second ECG signal;

determining whether the measured number of respirations per minute is greater than or equal to a predetermined number of respirations per minute;

displaying, on a display unit of the apparatus, information for inducing respiration of the subject until the number of respirations per minute reaches the predetermined number of respirations per minute, the information including the predetermined number of respirations per minute or a difference between the predetermined number of respirations per minute and the measured number of respirations per minute;

calculating a second blood pressure value based on the second calculated pulse transit time and the stored correlation equation, when the measured number of respirations per minute is greater than the predetermined number of respirations per minute, and outputting the calculated second blood pressure value; and measuring a third pulse transit time with the PPG and ECG sensors and calculating a third blood pressure value based on the third pulse transit time and the stored correlation equation, when the measured number of respirations per minute reaches the predetermined number of respirations per minute;

displaying, on the display unit, the first and third blood pressure values, after the measured number of respirations reaches the predetermined number of respirations.

9. The method of claim 8, further comprising:
calculating a heart rate based on the ECG signal or the pulse wave signal,
wherein the measuring of the number of respirations per minute comprises measuring the number of respirations per minute based on the heart rate.

10. The method of claim 8, wherein calculating the blood pressure value comprises:
calculating, by the controller, the blood pressure value by substituting the pulse transit time in the correlation equation, and
wherein when calculating the blood pressure value, the cuff is removed.

11. The method of claim 8, wherein displaying the information to induce respiration of the subject comprises:
displaying, on the display unit, contents corresponding to the information that induce respiration of the subject until the measured number of respirations per minute is greater than or equal to the predetermined number of respirations per minute.

12. The method of claim 8, wherein outputting the calculated blood pressure value comprises:

outputting, by the controller, a blood pressure measurement result including at least one of a blood pressure value measured before the respiration exercise and a blood pressure value calculated, when the measured number of respirations per minute is greater than or equal to the predetermined number of respirations per minute.

* * * * *